United States Patent
Deimling et al.

[11] Patent Number: 5,856,605
[45] Date of Patent: Jan. 5, 1999

[54] DEHYDROGENATION OF ETHYLBENZENE

[75] Inventors: Axel Deimling, Neustadt; Wilhelm Ruppel, Frankenthal; Uwe Behling, Bobenheim-Roxheim; Dieter Biedenkapp, Maxdorf, all of Germany

[73] Assignee: BASF Aktiengesellschaft, Ludwigshafen, Germany

[21] Appl. No.: 859,184

[22] Filed: May 20, 1997

Related U.S. Application Data

[63] Continuation of Ser. No. 404,715, Mar. 15, 1996, abandoned.

[30] Foreign Application Priority Data

Mar. 16, 1994 [DE] Germany .......................... 44 08 889.2

[51] Int. Cl.$^6$ .............................. C07C 5/367; C07C 5/32
[52] U.S. Cl. ............................................ 585/440; 585/446
[58] Field of Search ...................................... 588/440, 446

[56] References Cited

U.S. PATENT DOCUMENTS

| | | | |
|---|---|---|---|
| 2,683,180 | 7/1954 | Amos et al. | 260/440 |
| 3,100,807 | 8/1963 | Hatfield et al. | 585/440 |
| 4,229,603 | 10/1980 | Lyon | 585/444 |
| 4,769,506 | 9/1988 | Kosters | 585/440 |

FOREIGN PATENT DOCUMENTS

| | | |
|---|---|---|
| 2229132 | 6/1972 | Germany . |
| 231924 | 4/1980 | Germany . |
| 231924 | 1/1986 | Germany . |
| 765025 | 1/1957 | United Kingdom . |

Primary Examiner—Elizabeth D. Wood
Attorney, Agent, or Firm—Keil & Weinkauf

[57] ABSTRACT

A process for the dehydrogenation of ethylbenzene to styrene with input of heat by a heat-transfer medium on a dehydrogenation catalyst which is essentially located in a tube bundle, wherein the heat-transfer medium flows countercurrently to the reaction mixture in the region of the tube bundle, and, if required, another reaction chamber is located downstream of the tube bundle and is provided with a catalyst for adiabatic reaction.

2 Claims, 1 Drawing Sheet

DEHYDROGENATION OF ETHYLBENZENE

This application is a continuation of application Ser. No. 08/404,715, filed on Mar. 15, 1995 and now abandoned.

BACKGROUND OF THE INVENTION

Various processes have been disclosed for the industrial dehydrogenation of ethylbenzene to styrene (Ullmanns Encyklopädie der technischen Chemie, 4th edition, Vol. 22, page 298). In practical use is the adiabatic process which is usually carried out in two radial-flow reactors which are connected in series, with intermediate heating or feeding in of steam, and which are operated adiabatically, and the isothermal process in which a tube bundle reactor with indirect heat transfer is used. Steam is additionally used in this case too.

It is also known that the space-time yield of the isothermal process in simple tube bundle reactors in which only the tubes are filled with catalyst can be improved by having an adiabatic catalyst layer upstream (DE-A-1 059 437) or downstream (DE-A-1 290 130). DE-A-34 43 118 also describes a combination of an upstream and a downstream reaction zone operated adiabatically with a tube bundle reactor.

However, the feeding-in of a large amount of steam which has been preheated to a high temperature to initiate an adiabatic reaction has the disadvantage that precisely the advantage of the isothermal process, namely the operation with a low steam/ethylbenzene ratio is abandoned and part of the possible space-time yield is dispensed with.

SUMMARY OF THE INVENTION

It is an object of the present invention to increase further the space-time yield in tube bundle reactors operated isothermally, it being possible, but not necessary, to dispense with a preliminary adiabatic reaction.

We have found that this object is achieved by a process for the dehydrogenation of ethylbenzene to styrene with input of heat by a heat-transfer medium on a dehydrogenation catalyst which is essentially located in a tube bundle, wherein the heat-transfer medium flows countercurrently to the reaction mixture at least in the region of the tube bundle.

Thus, according to the invention, the reaction mixture is heated in the tube bundle indirectly with fuel gas using the countercurrent principle. While the gaseous reaction mixture is being passed through the tube bundle reactor, the reaction gradually starts up with the heating. The heating is sufficient for there to have been a considerable partial conversion at the end of the tube bundle reactor. However, it is possible with the countercurrent heating to provide simultaneous overheating of the reaction mixture so that there is still sufficient remaining energy present for a subsequent adiabatic reaction. It is possible in this way for the proportion of subsequent adiabatic reaction in the total reaction to be considerably larger than in the process described in DE 1 290 130 and it moreover takes place in the range of lowest pressure which is beneficial for selectivity. The part of the system which is operated adiabatically thus has a similar importance to the second reactor customary in the adiabatic process.

The invention thus achieves a combination of all the advantages of the known processes: the high selectivity of the adiabatic process, and the low steam/ethylbenzene ratio due to indirect heat input in the isothermal process. The process according to the invention is additionally distinguished in that three process steps, namely heating, first partial reaction in the tube bundle and subsequent reaction, can take place in a single apparatus.

The following experimental arrangement is used for the process example described hereinafter (see FIG. 1):

Figure 1:
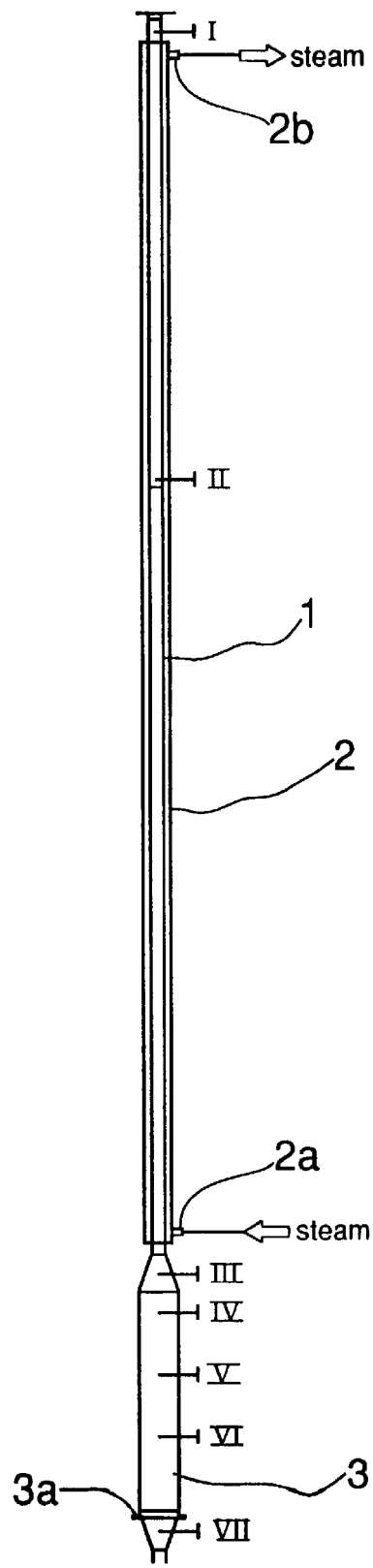
FIG. 1 shows a single tube (1) which is 5500 mm long and has an internal diameter of 78 mm, as used in tube bundles of industrial reactors, is surrounded by a jacket (2) which has top and bottom connectors (2a,2b) for introduction and removal of a heat-transfer medium, is fitted on top of a tubular reaction chamber (3) which is 1200 long and has a diameter of 163 mm and in which a grid (3a) is incorporated at the tapering point of the bottom (compare figure). Sample removal connectors (I-VII) are located at various heights.

The entire interior is filled with a commercial catalyst (G84C from Südchemie). The lower reaction chamber has no jacket and is used for the subsequent adiabatic reaction.

Steam and ethylbenzene are fed in from above, and the reaction mixture emerging at the bottom is condensed and investigated.

The result is as follows:

DESCRIPTION OF THE PREFERRED EMBODIMENTS

EXAMPLE

At a steam/ethylbenzene ratio of 1.25 kg/kg and a total cross-sectional loading in the tube part of 240 kmol/m$^2$h (steam+EB), an EB conversion of 64% and a styrene selectivity of 95.5 mol % are achieved at the end of the subsequent adiabatic layer. The pressure at the end of the reactor is 0.5 bar absolute. The temperature of the catalyst and of the reaction mixture at the entry to the apparatus is 420° C., at the end of the tube bundle 620° C. and at the end of the subsequent reaction layer 585° C.

We claim:

1. A process for the dehydrogenation of ethylbenzene to styrene comprising passing a reaction mixture of ethylbenzene and steam through a dehydrogenation catalyst, which is located in a tube bundle chamber, wherein a heat transfer medium flows counter-currently to the reaction mixture of ethylbenzene and steam, said heat-transfer medium heating the reaction mixture indirectly from a temperature of about 420° C. at the entry of the tube bundle chamber to about 620° C. at the end of the tube bundle chamber.

2. A process as defined in claim 1, wherein the reaction mixture passes through a further reaction zone, wherein a subsequent adiabatic reaction occurs.

* * * * *